United States Patent
Raptis et al.

(10) Patent No.: US 7,052,677 B1
(45) Date of Patent: May 30, 2006

(54) SUBSTITUTED OCTANUCLEAR PYRAZOLATO CLUSTERS WITH ELECTRON TRANSFER AND MRI CONTRAST AGENT PROPERTIES

(75) Inventors: Raphael Raptis, San Juan, PR (US); Peter Baran, San Juan, PR (US)

(73) Assignee: University of Puerto Rico, San Juan, PR (US)

( * ) Notice: Subject to any disclaimer, the term of this patent is extended or adjusted under 35 U.S.C. 154(b) by 0 days.

(21) Appl. No.: 10/600,267

(22) Filed: Jun. 20, 2003

Related U.S. Application Data (63) Continuation-in-part of application No. 09/470,504, filed on Dec. 22, 1999, now Pat. No. 6,596,259.

(60) Provisional application No. 60/113,537, filed on Dec. 22, 1998.

(51) Int. Cl.
*A61B 5/055* (2006.01)

(52) U.S. Cl. .................. 424/9.32; 424/1.11; 424/1.65; 424/9.1

(58) Field of Classification Search .............. 424/1.11, 424/1.65, 9.1, 9.3, 9.36, 9.32, 9.321; 548/300.1
See application file for complete search history.

(56) References Cited

U.S. PATENT DOCUMENTS

| | | | |
|---|---|---|---|
| 4,385,174 A | 5/1983 | Iqbal et al. | |
| 4,730,064 A | 3/1988 | Halbert et al. | |
| 5,141,855 A | 8/1992 | Schmittou | |
| 5,194,626 A | 3/1993 | Rolf et al. | |
| 5,364,953 A | 11/1994 | Beaty et al. | |
| 5,482,699 A | 1/1996 | Almen et al. | |
| 5,554,357 A | 9/1996 | Rajagopalan | |
| 5,614,168 A | 3/1997 | Berg et al. | |
| 5,624,662 A | 4/1997 | Unger et al. | |
| 5,850,086 A | 12/1998 | Que, Jr. et al. | |
| 5,892,033 A | 4/1999 | Komamura et al. | |
| 5,932,190 A | 8/1999 | Almen et al. | |
| 6,596,259 B1 * | 7/2003 | Raptis ....................... 424/9.32 | |

OTHER PUBLICATIONS

Stuart L. James, D. Michael P. Mingos, Andrew J.P. White and David J. Williams. Anion-templated formation of a unique inorganic 'super-adamantoid' cage $[Ag_6(triphos)_4(O_3SCF_3)4]^{2+}$ [triphos=$(PPh_2CH_2)_3CMe$]—*Chem. Commun.*, 1998. pp. 2323-2324. London, UK.

Vinod S. Nair, Karl S. Hagen; Iron Oxo Aggregation: $Fe_3$ to $Fe_6$ Synthesis, Structure, and Magnetic Properties of the Hexanuclear Dication $[Fe_6(\mu_4-O)_2(\mu_2-OMe)_8$ $(OMe)_4(tren)_2]^{2+}$, a Soluble, Crystalline Model of Iron Oxo Hydroxo Nanoparticles, the Core of Ferritin and Rust Formation; *Inorg. Chem*; Department of Chemistry, Emory University; vol. 31, pp. 4048-4050 (1992), Atlanta, Georgia.

Mario V. Capparelli, Paul Hodge, and Brian Piggott. X-Ray cristallographic structure of $Ga_8(pz)_{12}O_4Cl_4 2thf$: a novel gallium pyrazololate complex with a $Ga_4O_4$ core—*Chem. Commun.*, 1997. pp. 937-938.

Raphael G. Raptis, Irene P. Georgakaki, David C. R. Hockless; *Angew. Chem. Int. Ed.*, 38, No. 11, pp. 1632-1634 (1999).

Sergiu M. Gorun, Stephen J. Lippard; *Inorganic Chemistry*, vol. 30, No. 7, pp. 1625-1630 (1991).

F. Albert Cotton, L.M. Daniela, L. R. Falvello, J. H. Matonic, C. A. Murillo, X. Wang, H. Zhou; *Inorganica Chimica Acta 266*, pp. 91-102 (1997).

Wolfgang Micklitz, Stephen J. Lippard; *J. Am. Chem. Soc.*, 111, pp. 6856-6858 (1989).

Katerina Dimitrou, Jui-Sui Sun, Kirsten Folting, George Christou; *Inorg. Chem.*, 34, pp. 4160-4166 (1995).

F. Albert Cotton, Stan A. Duraj, Wiewlaw J. Roth; *Inorg. Chem.*, 23, pp. 4042-4045 (1984).

Martin K. Ehlert, Steven J. Rettig, Alan Storr, Robert C. Thompson, James Trotter; *Acta Cryst.* C-50, pp. 1023-1026 (1994).

Steven C. Shoner, Philip P. Power; *Inorg. Chem.*, 31, pp. 1001-1010 (1992).

Kingsley L. Taft, Andrea Caneschi, Laura E. Pence, Christopher D. Delfs, Georgia C. Papaefthymiou, Stephen J. Lippard; *J. Am. Chem. Soc.*, 115, pp. 11753-11766 (1993).

Kingsley L. Taft, Georgia C. Papaefthymiou, Stephen J. Lippard; *Science*, vol. 259, pp. 1302-1305 (Feb. 1993).

Kingsley L. Taft, Georgia C. Papaefthymiou, Stephen J. Lippard; Inorg. Chem., 33, pp. 1510-1520 (1994).

Hellmut Beinert, Richard H. Holm, Eckard Munck; *Science*, vol. 277, 1, pp. 653-659 (Aug. 1997).

Michael W. Willer, Jeffrey R. Long, Craig C. McLauchlan, R. H. Holm; *Inorganic Chemistry*, vol. 27, No. 2, pp. 328-333 (1998).

O. M. Yaghi, Z. Sun, D. A. Richardson, T. L. Groy; *J. Am. Chem. Soc.*, 116, pp. 807-808 (1994).

George M. Whitesides, John P. Mathias, Christopher T. Seto; *Science*, vol. 254, pp. 1312-1319 (Nov. 1991).

* cited by examiner

*Primary Examiner*—Dameron L. Jones
(74) *Attorney, Agent, or Firm*—Hoglund & Pamias, P.C.; Heath W. Hoglund (57) ABSTRACT

The present invention is directed to an Fe(III) complex comprising a redox-active metal cluster in a chemically inert shell. The inventive complex has electron transfer and paramagnetic properties.

18 Claims, 7 Drawing Sheets

SUBSTITUTED OCTANUCLEAR PYRAZOLATO CLUSTERS WITH ELECTRON TRANSFER AND MRI CONTRAST AGENT PROPERTIES

This application is a continuation-in-part of application Ser. No. 09/470,504, filed Dec. 22, 1999, now Pat. No. 6,596,259, which claims the benefit of U.S. Provisional Application No. 60,113,537, filed Dec. 22, 1998.

GOVERNMENT INTERESTS

The claimed invention was made with Government support under grant No. 5506GM08102-30S1 awarded by the National Institute of Health (NIH). The Government has certain rights in this invention.

FIELD AND BACKGROUND OF THE INVENTION

This invention relates to a metal-based cubane structure contained in an octanuclear complex which can be used as an paramagnetic agent and/or an electron-transfer agent. Paramagnetic compounds are useful for a wide variety of applications. One particular use is as a contrast agent for magnetic resonance imaging (MRI). Generally the contrast agent is injected or otherwise diffused within the subject of observation. When the target is then scanned by an MRI machine, the areas containing the contrast agent appear brighter (or darker) because of its paramagnetic properties. Electron-transfer agents also are useful for a wide variety of applications. Some particular uses are: as molecular junctions, oxidation catalysts, electron acceptors in chemosensors and photovoltaic systems.

More specifically, this invention is directed to a redox-active metal-based structure, protected inside an inert coating. This complex, which can be defined as $Fe_8(\mu_4\text{-}O)_4(\mu\text{-}4\text{-}R\text{-}pz)_{12}L_4$, is stable over several oxidation states. The present invention is also directed to a method of making this product from simple starting materials.

Thermodynamic stability is a desired property of materials to be used in most commercial applications. At the same time, however, chemical versatility is typically required for the manifestation of interesting properties or catalytic activity. A combination of these contrasting characteristics is typically achieved by the coating of large surfaces or particles with inert substances, at the macroscopic and microscopic scale, respectively. Such structures are known to naturally occur at the macromolecular level when, for example, metal active centers are protected inside the organic part of metalloproteins.

The complex encompassed by the present invention has a core, which is the source of redox properties, encapsulated in a protective shell. Such a complex provides an ideal building block for the construction of one-, two- and three-dimensional materials. These materials can be constructed by connecting or bonding units of the complex made in accordance with the present invention by bridging atoms or groups. The bridges can be either bidentate ligands, which replace terminal atoms, or bifunctional substituents, which connect the units through substitution at the 3-, 4- or 5-position of their respective pyrazoles. The advantage of using the inventive complex for the construction of these materials, instead of a single metal atom, or other mono- or polynuclear products, is that the complex can withstand redox manipulation without significant geometrical changes, which would cause the structure of the material to collapse.

The invention discovers that the structural integrity of the present complex is a function of the way it is composed. Specifically, the desired redox properties are a function of the metal core, while the connections required for the construction of the above proposed materials take place at the outer inert shell. Accordingly, construction of 1-, 2- and 3-dimensional materials leaves the core unaffected. Similarly, redox changes in the core leave the outer structure unaffected. In addition, when the metal atoms employed are paramagnetic, the complexes encompassed in the invention are also paramagnetic, or can become paramagnetic in one of their oxidation states. The materials which will be prepared from the inventive complex will have all the magnetic and redox properties of this building unit, possibly even amplified.

The invention surprisingly and unexpectedly demonstrates that by encapsulating a redox active core inside an inert protective coating, the resulting material retains structural stability over several oxidation states. This result is achieved by separating the center of redox activity, the core, from the outer surface of the molecule, the coating. In some cases, the molecular symmetry of the complexes $Fe_8(\mu_4\text{-}O)_4$ $(\mu\text{-}4\text{-}R\text{-}pz)_{12}L_4$ allows the existence of optically active forms, which can be prepared as racemic mixtures or enantiomerically enriched or enantiomerically pure forms.

SUMMARY OF THE INVENTION

To achieve the beneficial properties of stability and versatility previously described, the present invention is directed to molecules having an active center coated with inert substances. More specifically, the present invention is directed to a complex comprising redox-active metal clusters protected inside a chemically inert shell. The invention is also directed to the generation of four additional forms of the complex through electrochemical reduction of the inventive complex. In addition, the present invention is directed to methods of using these structures as building blocks for the construction of durable supercluster assemblies having electron-transfer properties. The invention is further directed to uses of this coplex as a dopant in materials, i.e., polymers to impart magnetic or electrical properties to the doped material. The inventive complex may also be used as a contrast agent in magnetic resonance imaging (MRI) applications, for example.

Pyrazolates are convenient bridging ligands or complexing agents for the synthesis of polynuclear products which, due to the aromatic character of the ligand or complexing agent, the chemical activity is restricted to the metal centers.

One aspect of the present invention is directed to a material represented by the formula (1):

$$Fe_8(\mu_4\text{-}O)_4(\mu\text{-}4\text{-}R\text{-}pz)_{12}L_4 \qquad (1)$$

where:

Fe is in the +2, +3 or +4 oxidation state, or two different oxidation states.

$\mu_4$-O represents a quadruply bridging oxygen atom;

$\mu$-4-R-pz represents a bridging pyrazolate ligand substituted at the 4 position by a group R, where R is any atom or group of atoms attached by a single bond to the pyrazole, for example organic groups, halogens, alkyls, aryls and other examples given below;

L is any terminal ligand, such as and for example only F, Cl, Br, NCO, NCS, alkyl, aryl or any anionic or neutral ligand or any combination of four terminal ligands.

The inventive complex can be in a racemic, an enantiomerically-enriched or an enantiomerically-pure form.

More preferably, formula (1) represents a Fe(III)-complex designated as:

Fe$_8$($\mu_4$-O)$_4$($\beta$-pz)$_{12}$Cl$_4$ where:

pz represents a pyrazolato anion, C$_3$H$_3$N$_2$, and $\mu$ represents a bridging group, i.e., a bridging pz, or a bridging atom, such as an oxygen atom. The Fe(III) complex optionally has T-symmetry.

The invention has unexpectedly demonstrated that the inventive Fe(III) complex contains a redox-active Fe$_4$O$_4$ core, protected inside a Fe-pyrazolate coating, which is stable over five oxidation states. The Fe$_4$O$_4$-core of the Fe(III) complex is the first example of an all-ferric/oxygen cubane complex. Consistent with the +3 valence of this Fe(III) complex are the shorter Fe—O bonds of formula (1), i.e., 2.040(4) Å average, compared to those of its lower-valence analogues.

As stated, the invention also demonstrates that the complex defined by formula (1) is stable over several, preferably five, oxidation states. Stability is defined as the ability of the complex of formula (1) to retain the structure and stoichiometry of its neutral form when it is reduced by one, two, three or four, one-electron processes. In other words, the inventor has discovered that the species represented by (1), (1)$^{-1}$, (1)$^{-2}$, (1)$^{-3}$ and (1)$^{-4}$ are thermodynamically stable under the electrochemical reduction of the complex of formula (1). Moreover, the invention also demonstrates that these properties do not change with substitution on the 4 position of the pyrazole or the terminal ligand. In addition, while the compound retains four redox steps, the potential of such steps can be tuned by the use of different substituents.

The present invention also demonstrates that manipulation of the solubility of the inventive complex is possible through substitution at the outer shell. This can be done through substitution at either the positions of the terminal ligands, or the 4-position of the pyrazoles. While the preferred form of the complex is hydrophobic, i.e., insoluble in water, but soluble in a large number of organic solvents, it can easily become water soluble by attaching hydrophilic groups to its surface through such substitutions. Water-soluble derivatives of the inventive complex may find medicinal use, either in therapeutic or diagnostic applications, for example, as MRI contrast enhancing agents.

The inventive complex, when manipulated in the above stated manner to make it physiologically acceptable, allows the complex to be used in a method of generating a magnetic resonance image (MRI) of a mammal. Such a method comprises administering to a mammal, in an amount effective to provide a MRI image, a contrast agent comprising the complex of formula (1).

Additionally, the present invention demonstrates that the complex defined by formula (1) can be assembled in a single reactor from simple starting materials that are commercially available.

DETAILED DESCRIPTION OF THE INVENTION

Preparation of Fe(III) Complexs

Example 1

Fe$_8$($\mu_4$-O)$_4$($\mu$-4-R-pz)$_{12}$L$_4$, R=H and L=Cl:

The starting materials that can be used to prepare the Fe$_8$(P$_4$-O)$_4$($\mu$-pz)$_{12}$Cl$_4$ complex defined by formula (1) include the following commercially available materials: anhydrous ferric chloride (FeCl$_3$), pyrazole (C$_3$H$_4$N$_2$, pzH) and triethylamine. Also, sodium pyrazolate (Na-pz), or potassium pyrazolate (K-pz) can be readily prepared from pyrazole and sodium hydride or potassium hydride. Either pyrazolate works equally well. Other common reagents can be used as pyrazolate-transfer agents in the preparation of formula (1).

A typical preparation of the example is as follows: To a suspension of FeCl$_3$ (3.120 g; 19.23 mmol) in CH$_2$Cl$_2$ (200 mL) was added solid Napz (2.598 g; 28.85 mmol) under an Ar atmosphere with stirring. To the resulting dark brown solution, triethylamine (1.340 mL; 9.617 mmol) was added dropwise with stirring under argon. After 20 h, the dark brownish-red reaction mixture was exposed to air, sealed again and kept stirring for an additional 24 h period. After filtration, an unidentified dark brown solid (a minor product) was disposed and the dark red filtrate was allowed to slowly evaporate to dryness at 23° C. under air. The resulting solid was washed with acetone (50 mL) and recrystallized twice from CH$_2$Cl$_2$ (140 mL and 70 mL). A dark red crystalline solid was collected by filtration, washed with methanol, and dried. Yield: 1.07 g (30%). (b) To a suspension of FeCl$_3$ (0.910 g; 5.61 mmol) in CH$_2$Cl$_2$ (43 mL) prepared under an argon atmosphere was added solid pyrazole (1.146 g; 16.83 mmol) under air with stirring. An orange crystalline solid of Fe(pzH)$_3$Cl$_3$ was formed within 60 seconds. Triethylamine (1.955 mL; 14.03 mmol) was added dropwise with stirring. All orange solid has dissolved and reaction mixture turned dark red. After stirring for 13 hours a dark brownish-red mixture was filtered. Solid portion was disposed and the resulting dark red solution was let to evaporate slowly to dryness at 23° C. The resulting solid was extracted with methanol (10 mL) and recrystallized from CH$_2$Cl$_2$ (22 mL) under air. The obtained dark red crystalline solid (0.469 g) was recrystallized from another portion of CH$_2$Cl$_2$ (15 mL) under the nitrogen atmosphere. Big dark red crystals were collected by filtration, washed with methanol, and dried.

Example 2

$Fe_8(\mu_4\text{-}O)_4(\mu\text{-}4\text{-}R\text{-}pz)_{12}L_4$, R=Cl and L=Cl:

A typical preparation of the example is as follows: To a suspension of $FeCl_3$ (0.197 g; 1.21 mmol) in $CH_2Cl_2$ (30 mL) prepared under an argon atmosphere was added solid 4-Cl-pyrazole (0.374 g; 3.64 mmol) under air with stirring. To the pale red solution was added dropwise with stirring triethylamine (0.423 mL; 3.04 mmol). After stirring for 5 min a dark red mixture was filtered and liquid part was placed into a Schlenk tube and stirred under nitrogen for 2 days, when the stirring was interrupted. In 2 months, regular octahedral dark orange crystals of the product together with colorless needles of triethylammonium chloride were collected. One of the orange crystals was used for the x-ray study. Then the solid mixture was recrystallized from acetone (15 mL), and subsequently from $CH_2Cl_2$ (4 mL). Product was collected by filtration, washed with methanol, and dried.

Example 3

$Fe_8(\mu_4\text{-}O)_4(\mu\text{-}4\text{-}R\text{-}pz)_{12}L_4$, R=Me and L=Cl:

A typical preparation of the example is as follows: To a suspension of $FeCl_3$ (0.967 g; 5.96 mmol) in $CH_2Cl_2$ (200 mL) prepared under an argon atmosphere was added dropwise 4-Me-pyrazole (1.48 mL; 17.9 mmol) under air with stirring. To the pale red solution was added dropwise with stirring triethylamine (2.08 mL; 14.9 mmol). After stirring for 20 hours a dark orange mixture was filtered.

Example 4

$Fe_8(\mu_4\text{-}O)_4(\mu\text{-}4\text{-}R\text{-}pz)_{12}L_4$, R=H and L=Br:

A typical preparation of the example is as follows: To a suspension of $FeBr_3$ (0.371 g; 1.26 mmol) in $CH_2Cl_2$ (15 mL) prepared under an argon atmosphere was added solid pyrazole (0.256 g; 3.77 mmol) under air with stirring. To the red solution was added dropwise with stirring triethylamine (0.437 mL; 3.14 mmol). After stirring for 10 min the mixture was filtered and filtrate was placed into a Schlenk tube and stirred under nitrogen for 6 days. The volume of the reaction mixture was reduced to 5 mL under vacuum, stirred overnight and filtered under nitrogen. The filtrate was evaporated to dryness, extracted with methanol (22 mL) and recrystallized from diethyl ether (40 mL) and subsequently from $CH_2Cl_2$ (6 mL). Product was collected by filtration, washed with methanol, and dried.

Other Examples:

Preparation of other Fe(III) complexes can be obtained by substitution of the terminal ligand Cl or Br, and/or by substitution on the 4 position of the pyrazole groups. Specifically, the terminal ligands can be substituted by F, Br, SCN, OCN, OPh (where Ph is a phenyl group either substituted or unsubstituted, i.e., $C_6H_5$, $C_6H_4R$, $C_6H_4X$), py (where py is a pyridine group, $C_6H_5N$, or substituted pyridine group, i.e., $C_6H_4NR$, $C_6H_4NX$), or a metal or metal complex such as Az, Cu, $PdCl_2$ or $PtCl_2$. Alternatively, the terminal ligand can be substituted by a bridging ligand including pyrazine, or bipyridine. With the substitution of bridging ligands multiple Fe(III) complexes are joined.

Figure 7:
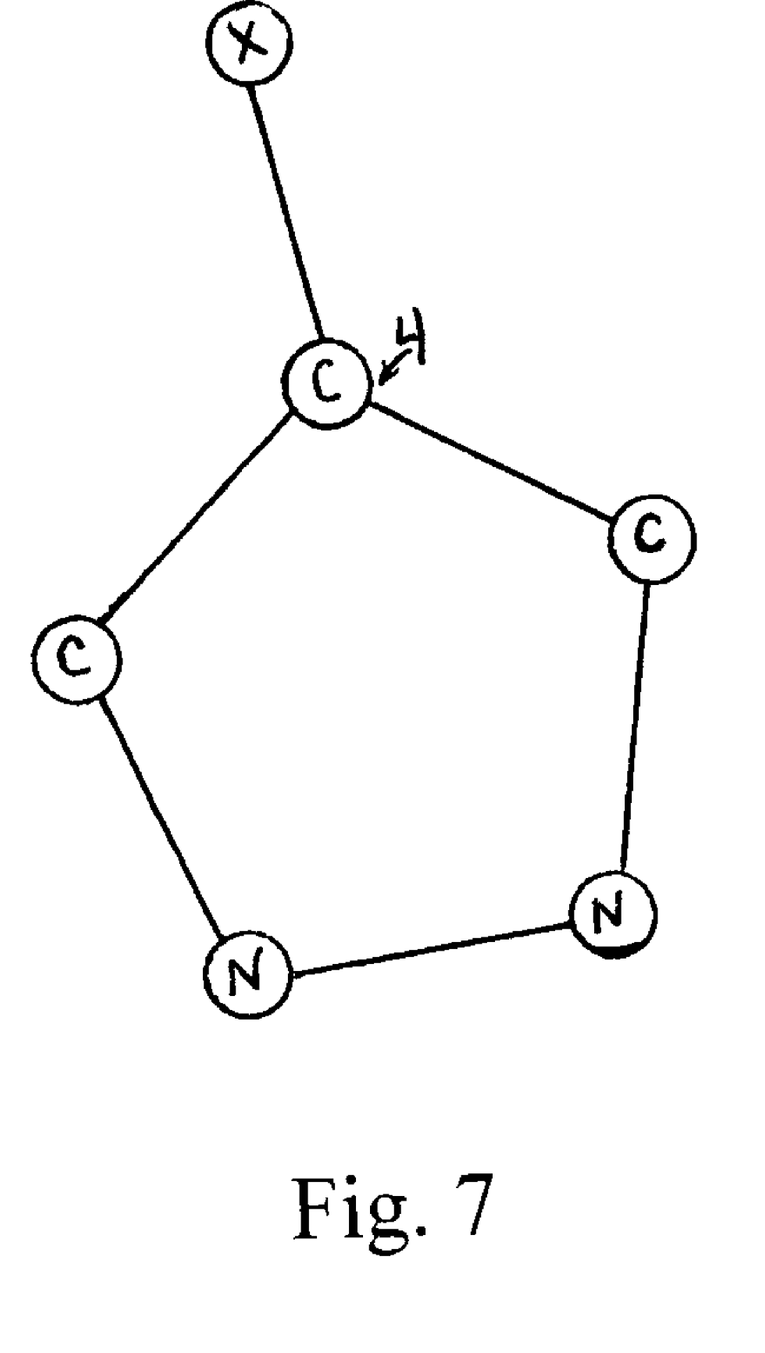
FIG. 7 illustrates a pyrazolato group.

The 4 position of the pyrazole groups are substituted as shown in FIG. 7. Specifically, the 4 position is substituted by a halogen (including, e.g., F, Cl, Br, I) or a pseudo-halogen (including, e.g., CN). Alternatively, the 4 position is substituted by an organic group, which include all variations of $C_nH_{2n+1}$, $C_nH_{2n-1}$, $C_nH_{2n-3}$, $C_nH_{2n}X$, $C_nH_{2n-2}X$, $C_nH_{2n-4}X$ where n is less than 40 and where X is selected from the group consisting of F, Cl, Br, I, CN, OH, $NH_2$, CHO. As used hereinafter, a bridging pyrazolato group comprises any pyrazole either substituted or unsubstituted.

As further described below, a compound according to formula (1) is very stable in a variety of solvents, temperatures and chemical reagents. It can be safely refluxed in organic solvents and used in neutral and alkaline solutions. It withstands treatment with oxidants up to 1.6 Volts (versus $Fc/Fc^+$, Fc=ferrocene), while its is easily and reversibly reduced to $1^-$, $1^{-2}$, $1^{-3}$ and $1^{4-}$ retaining its structural integrity upon treatment with reducing agents, such a tetrabutylammonium borohydride. This point has been proven by the X-Ray structural characterization of the first one-electron reduced derivative of (1), $[Fe_8(\mu_4\text{-}O)_4(\mu\text{-}pz)_{12}Cl_4]^-_1$, $(1)^-$. The latter has a structure practically identical to (1) with only minor variation in the Fe—Cl and Fe—O bond lengths.

Analysis of Fe(III) Complexes

The larger crystals made according to the first example above were used for a single crystal X-ray structure determination, while the smaller ones were used for all other analyses. Analyses performed on the crystals grown from the $CH_2Cl_2$ solution of formula (1) produced the following results.

Elemental Properties:

The precipitated crystals exhibited a melting point of approximately 565 K, as determined by DTA analysis. The analyses for C, H, N and Cl were performed gravimetrically by an elemental analyzer. The analysis for Fe was done by Atomic Absorption spectroscopy (flame atomization). The analyses of all five elements show the w/w% of the element in a sample of formula (1)-½ hexane. The first number reported is the measured weight percent of the element, averaged from duplicate runs, while the second number (in parenthesis) is the theoretically calculated value for formula (1)⁻·½ hexane. The fact that the measured value is so close to the theoretical value evidences the correctness of the characterization given below:

C=31.14 (31.19),

H=2.81 (2.87),

N=21.59 (22.39),

Cl=9.62 (9.45),

Fe=29.43 (29.76).

Spectroscopic Properties:

The electronic spectrum of formula (1) in a $CH_2Cl_2$ solution, recorded in the UV/Vis/NIR region, revealed a $\lambda_{max}$=359 nm, consistent with the red color of the material.

A powdered sample of formula (1) formed into a KBr pellet showed the following IR absorption peaks (where the peak intensity was denoted as vs=very strong, s=strong, m=medium and w=weak) in $cm^{-1}$, using a KBr disk: 1490m, 1417m, 1362s, 1268s, 1169s, 1145m, 1078w, 1045vs, 963w, 915w, 894w, 763s, 615m, 555m and 476s. With a polyethelene pellet of formula (1), three additional IR absorption peaks were observed at 349s, 331s and 308s.

The mass spectrum of formula (1) was recorded by the Fast Atom Bombardment technique and the following m/z peaks were observed (the fragment to which they are attributed in parenthesis): 1457.6 (M+), 1420.6 (M—Cl+), 1388.5 (M-pz+), 1353.6 (M—Cl,pz+), 1321.5(M−2pz+), 1286.5 (M−2pz,Cl+).

Figure 4:
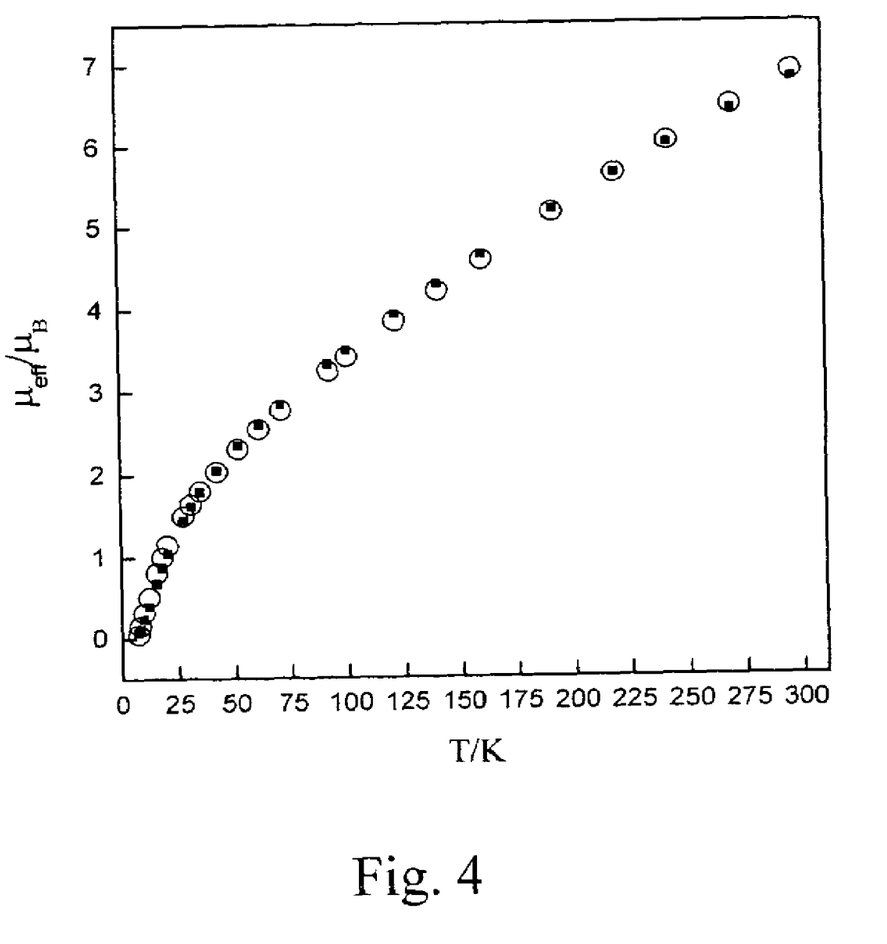
FIG. 4 illustrates the magnetic moment versus temperature of a complex of formula (1).
Figure 5:
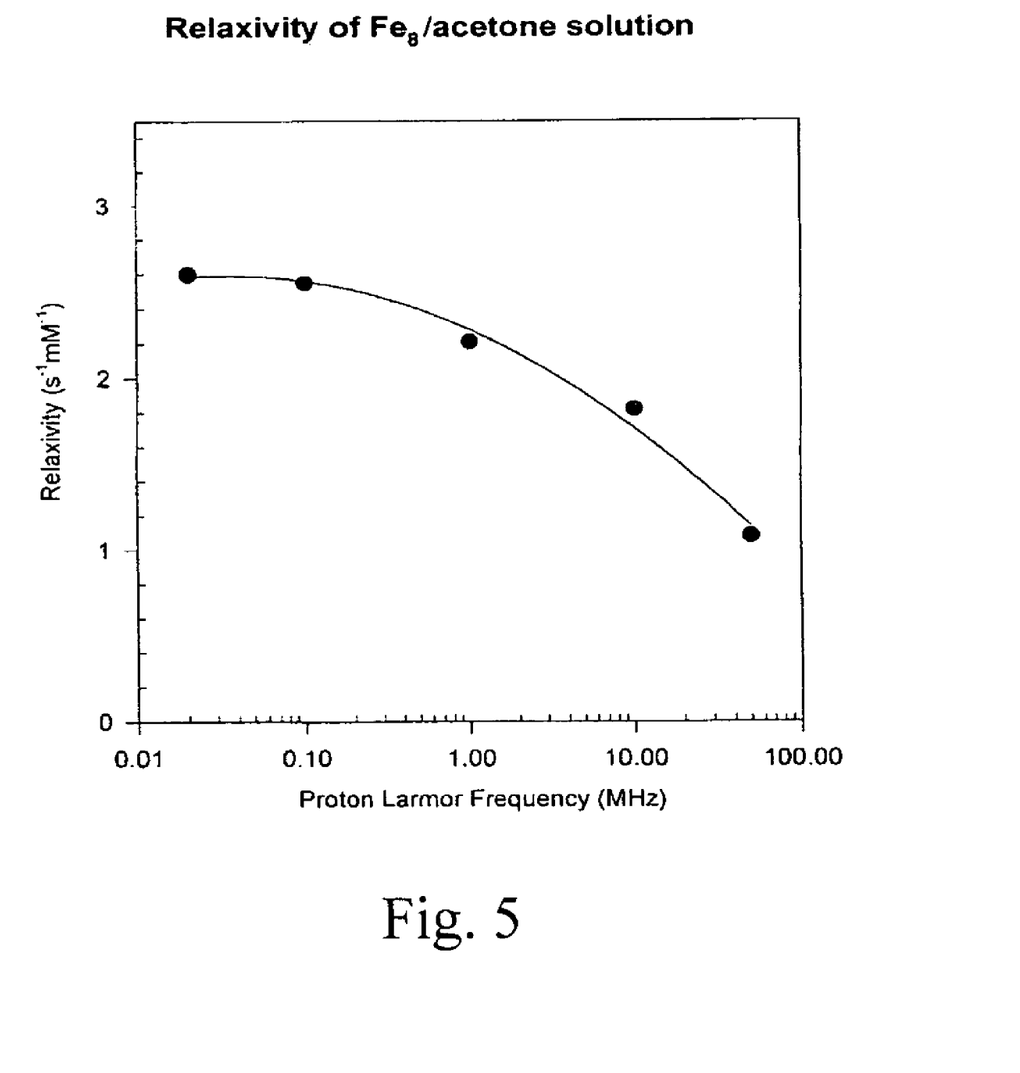
FIG. 5 illustrates the proton relaxivity versus proton Larmor frequency plot of a complex of formula (1).
Figure 6:
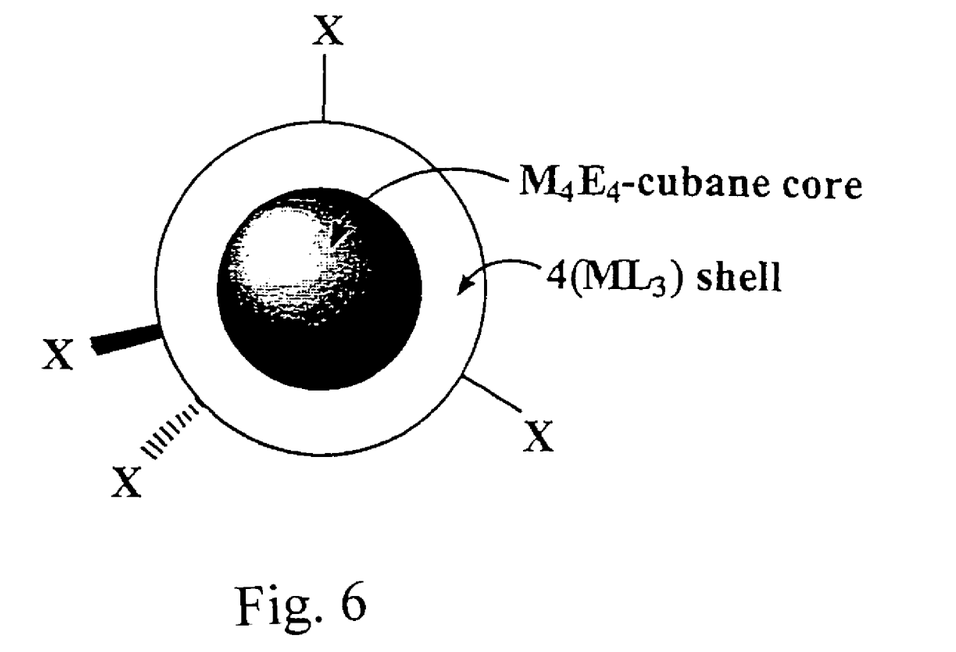
FIG. 6 illustrates an octanuclear complex containing a metal cubane core in an inert shell.

Magnetic Properties:

Magnetic moment: $\mu_{eff}$=6.52 B.M., calculated from a Faraday balance susceptibility measurement at 290 K. The compound according to formula (1) is diamagnetic at its ground state, but paramagnetic at temperatures above 4 K, with its magnetic moment increasing steadily up to 300 K (the limit of our study) without reaching saturation (FIG. 4). As a consequence of its paramagnetism, compound according to formula (1) shows good proton-relaxivity properties, qualifying it as a potential Contrast-Enhancing Agent for Magnetic Resonance Imaging (MRI), as shown in FIG. 5.

Crystallographic Properties:

Red parallelepiped crystals appropriate for X-ray diffraction study were grown from the $CH_2Cl_2$/hexane solution of formula (1). A Rigaku-A-FC6S diffractometer employing a Mo—Ka=0.71069 Å beam source showed the following cell parameters for the primitive triclinic cell, P $\bar{1}$ (No. 2), characteristic of the crystals (with standard deviation in parenthesis): a=12.367(5), b=12.508(5), c=20.794(4) Å, α=77.45(3), β=80.80(3), γ=70.27(3)°, V=2942(2) Å³, Z=2, $d_{calc}$=1.694 g/cm, μ=21.53 cm$^{-1}$.

Figure 1:
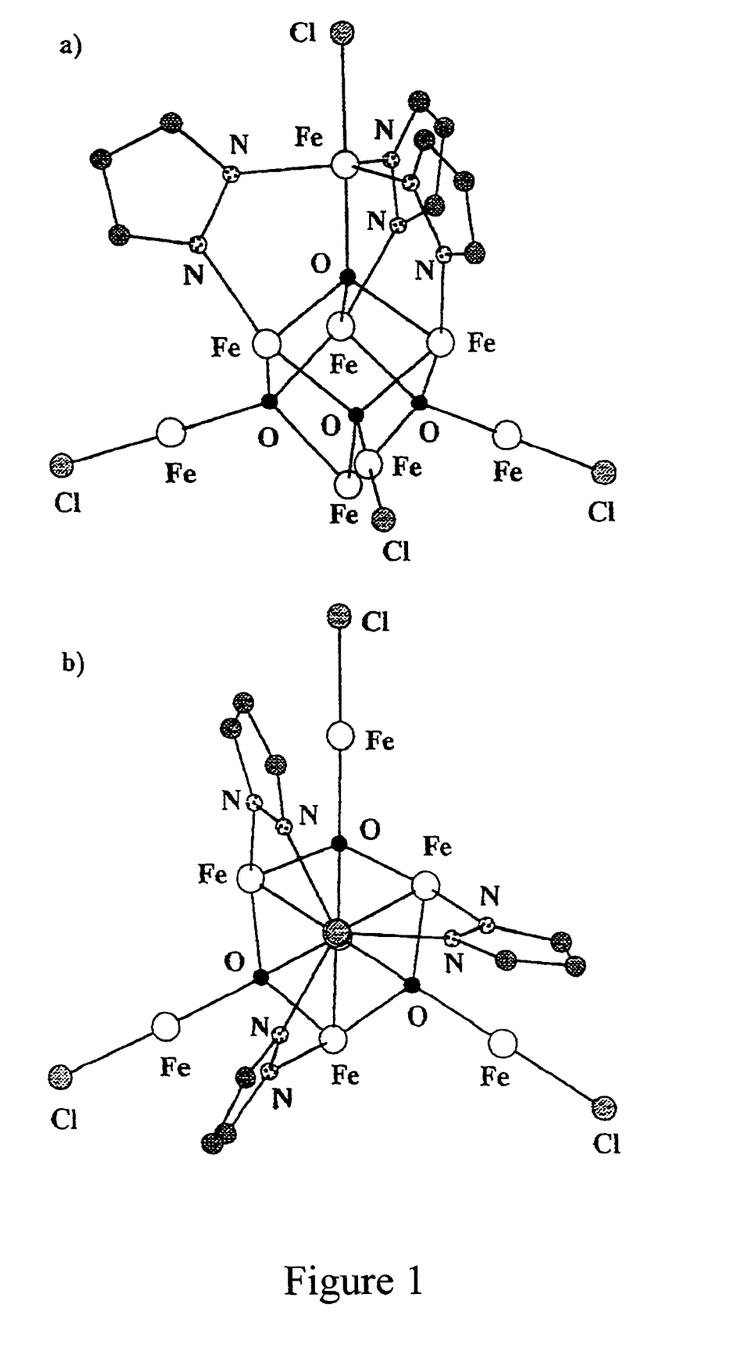
FIG. 1a) illustrates a side view of the Fe$_8$O$_4$Cl$_4$ part of a complex of formula (1), and of three of the twelve pyrazolato groups therein.
FIG. 1b) illustrates the same as 1a, but is viewed down a C$_3$-axis.

FIG. 1 illustrates the crystal structure for the $Fe_4O_4$-cube. Specifically, the bond lengths were found to be (with the standard deviation in parenthesis): Fe—O=2.022(4)–2.056(4) Å; Fe—Fe=3.059(1)–3.088(1) Å; Fe—N=2.048(5)–2.070(5) Å; Fe—O—Fe= 97.1(2)–98.7(2) Å; O—Fe—O=81.1(2)–82.4(1) Å; For the outer Fe-atoms: Fe—O=1.944(4)—1.963(4) Å; Fe—Cl=2.267(2)–2.276(2) Å; Fe—N=2.007(5)–2.025(5) Å; N—Fe—N=114.2(2)–124.6(2) Å; Fe—N—N=119.1(4)–121.6(4) Å.

The crystallographic characterization of formula (1) was performed using well-established procedures. In analyzing the crystal structure data, corrections were made for Lorentz and polarization effects using an empirical absorption factor based on azimuthal scans, which resulted in a reliability factor of R=0.036, and a goodness-of-fit indicator of 1.73.

The eight Fe-atoms associated with formula (1) were located on $C_3$-axes at positions defining two concentric tetrahedral with average Fe—Fe edges of 3.074(2) and 5.853(4) A, respectively. The $\mu_4$-O atoms, which connected the eight-Fe-atom network, were expected to be efficient mediators of antiferromagnetic coupling and expected to account for the relatively low effective magnetic moment of 6.52 B.M. of formula (1). Within each ($\mu_4$-O)$Fe_4$ group, the O-atoms were displaced from the centers towards the bases of the $Fe_4$-trigonal pyramids.

Figure 2:
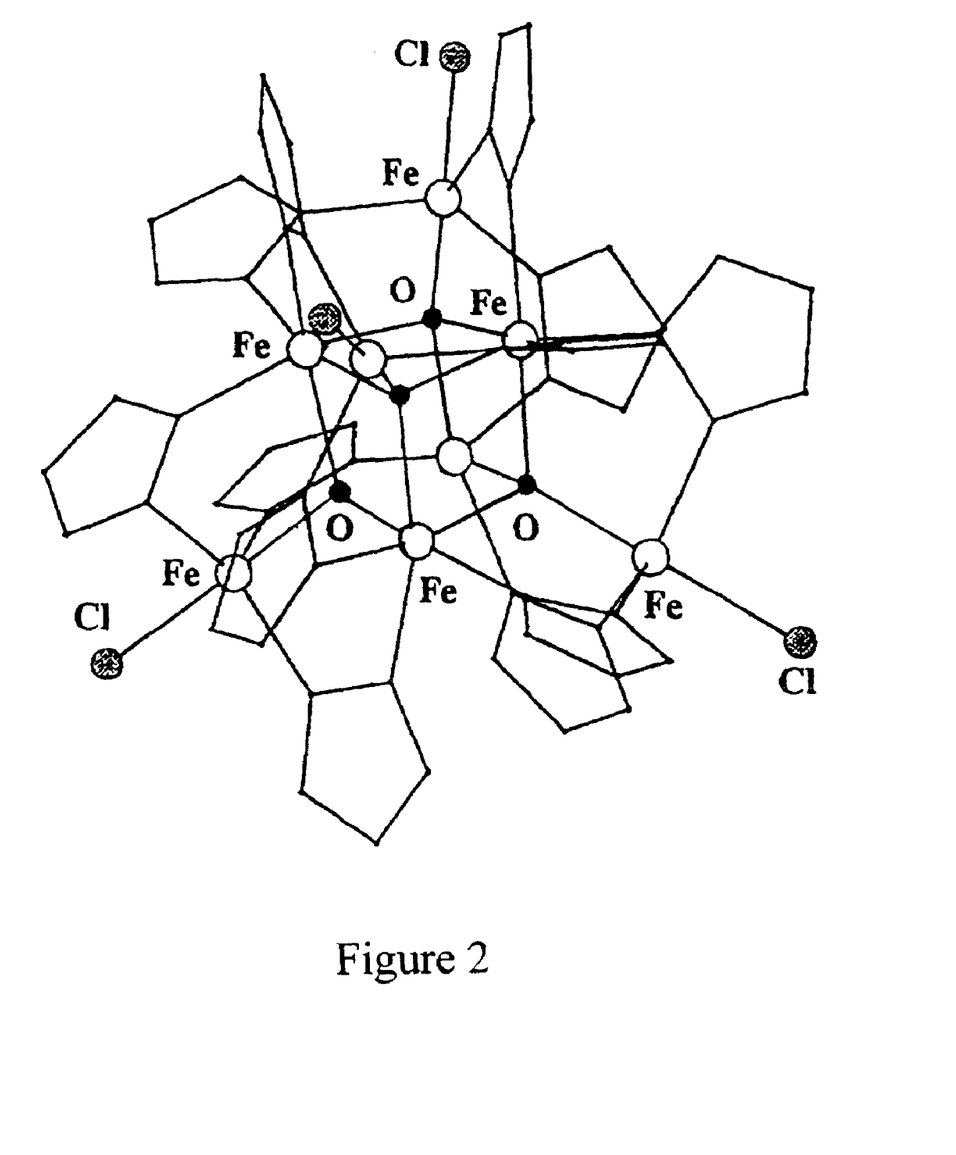
FIG. 2 illustrates the structure of a complex of formula (1) comprising spherical atoms of arbitrary radii. Hydrogen atoms are not shown.

While the $Fe_8O_4Cl_4$ skeleton of formula (1) was in tetrahedral arrangement, the propeller-like rotation of the μ-pz groups eliminated the mirror planes of Td symmetry, thus reducing the overall symmetry of formula (1) to that of the T-point group. A consequence of this symmetry was that formula (1) occurred in two enantiomeric forms; first co-crystalized as a racemic mixture (i.e., a 50/50 mixture of the two possible enantiomeric forms), the interconversion of which requires the rearrangement of all twelve pyrazolato bridges by simultaneous rotation about the four $C_3$-axes of 1. The arrangement of twelve pyrazole rings in the outer part of formula (1) gave this molecule an approximate appearance of a sphere of approximately 12 Å diameter and a hydrophobic surface responsible for its high solubility in non-polar solvents (FIG. 2). FIG. 2 shows on enantiomeric form, while the other form is its mirror image.

Figure 3:
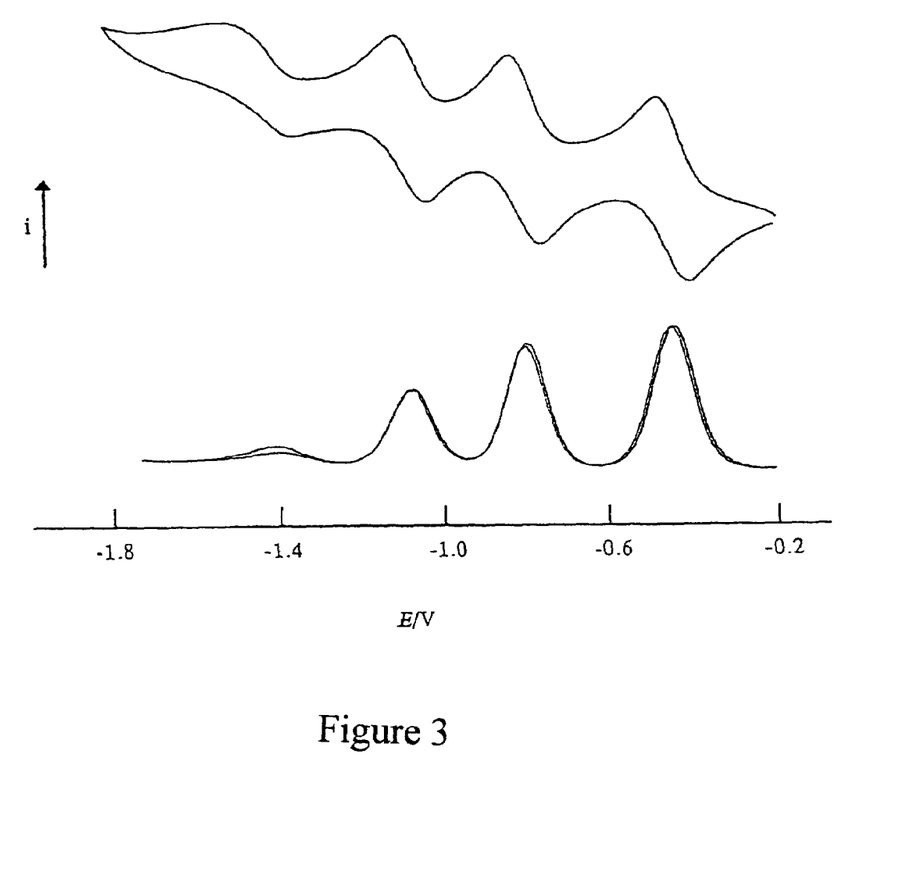
FIG. 3 illustrates voltammetry of a complex of formula (1) in 0.1 M Bu$_4$NPF$_6$/PrCN, with a scan speed =100 mV/sec, T=223 K, Pt-disk working electrode, versus Fc/Fc+, wherein the upper trace represents a cyclic voltammogram, and the lower trace represents a cyclic AC-scan.

Electrochemical Properties:

The electrochemical properties of the complex of the invention were studied by Cyclic and AC Voltamemetric techniques, in $CH_2Cl_2$ solvent, 0.5 M terabutylammonium hexafluorophosphate supporting electrolyte, in a voltammetric cell with the standard three-electrode configuration, employing a platinum working electrode. The electrochemical study, from −2.00 to +2.20 V, showed three reversible reductions at −0.43, −0.78 and −1.07 V vs. Fc/Fc+. A fourth reduction at −1.38 V was irreversible at 285 K, but became chemically reversible and electrochemically quasi-reversible in chilled solution (FIG. 3).

As no oxidation was observed, it was evident that the complex of formula (1) retained its structural integrity, in its neutral or some anionic form, over the measured 4.20 V window, i.e., −2.00 to +2.20V. The complete electrochemical reversibility of the first three reductions, at ambient or low temperature, indicates that no significant structural rearrangement accompanied those electron-transfer processes. The unusual stability of formula (1) over five oxidation states can be accounted for by the encapsulation of the $Fe_4O_4$-core inside the outer shell of four interlocked Fe(μ-pz)$_3$Cl groups forcing its structural integrity, in a fashion similar to the wrapping of apoferritin around the Fe/O cluster of ferritin. The spontaneous assembly from mononuclear precursors, as well as the stability and rich electrochemistry of formula (1), indicate the likelihood of existence of an electron-transfer protein based on a $Fe_4O_4$ active center described in formula (1).

The four tetrahedrally arranged chlorine atoms at the outer shell of formula (1) were readily substituted by anionic or neutral ligands in simple metathesis reductions providing a convenient means by which to manipulate the size and solubility of the octanuclear cluster, as well as to connect octanuclear units by bridging ligands into covalent supramolecular assemblies. Such derivative formula (1) retained the redox characteristics of their parent compound with small variations of the $E_{1/2}$ values. These results indicate that the $Fe_4O_4$-core was the site of the redox activity. Accordingly, the above described derivatives (made by substitutions to formula (1)) likewise are suitable to act as electron transfer agents, and as paramagnetic compounds.

Similarly, complete structural characterizations for the complexes $Fe_8(\mu_4$-O$)_4(\mu$-4-R-pz$)_{12}L_4$, where L=Br, NCO, NCS, R=Cl, Br, I, $CH_3$, $CH_2CH_2Cl$, and $Fe_8(\mu_4$-O$)_4(\mu_4$-R-pz$)_{12}$(NCS)$_3$Cl show that these complexes have the same octanuclear structure as example one, only with changed substituents. These other complexes show the same electrochemical and magnetic properties as example one.

We claim:

1. A Fe(III) complex having paramagnetic and electron transfer properties comprising an iron cluster in a chemically inert shell, wherein said iron cluster comprises a $Fe_4O_4$ cubane core which is stable over five oxidation states and wherein said chemically inert shell comprises four iron atoms and twelve bridging pyrazolato groups.

2. The Fe (III) complex of claim 1, wherein said complex comprises a contrast agent.

3. A paramagnetic compound having the formula:

where the portion of the compound identified as $\mu_4$-O is a quadruply bridging oxygen atom and u-pz is a bridging pyrazole ring, and the portion of the compound identified as L is a ligand.

4. The paramagnetic compound of claim 3, wherein said compound comprises a contrast agent.

5. The paramagnetic compound of claim 3, wherein said compound has electron transfer properties.

6. The paramagnetic compound of claim 3, wherein said bridging pyrazole rings each comprise a halogen or pseudo-halogen attached at the 4 position of the bridging pyrazole ring wherein said halogen or pseudo-halogen is selected from the group consisting of F, Cl, Br, I and CN.

7. The paramagnetic compound of claim 3, wherein said bridging pyrazole rings each comprise an organic substituent attached at the 4 position of the bridging pyrazole rings wherein said organic substituent is selected from group consisting of $C_nH_{2n+1}$, $C_nH_{2n-1}$, $C_nH_{2n-3}$, $C_nH_{2n}X$, $C_nH_{2n-2}X$, $C_nH_{2n-4}X$ where n is less than 40 and where X is selected from the group consisting of F, Cl, Br, I, CN, OH, $NH_2$, CHO.

8. The paramagnetic compound of claim 7, wherein n is less than 20.

9. The paramagnetic compound of claim 3, wherein said bridging pyrazole rings each comprise an aryl group attached at the 4 position of the pyrazole ring.

10. The paramagnetic compound of claim 3, wherein said ligand is selected from the group consisting of F, Cl, Br, SCN, OCN, OPh, Ph, and py, where Ph is a phenyl group and py is a pyridine group.

11. A Fe(III) complex having paramagnetic and electron transfer properties comprising a metal cluster in a chemically inert shell, wherein said metal cluster forms a cubane core having the formula $Fe_4O_4$ and is stable over five oxidation states.

12. The Fe(III) complex of claim 11, wherein said chemically inert shell comprises four iron atoms, twelve bridging pyrazolato groups and four ligands.

13. The Fe(III) complex of claim 12, wherein said twelve bridging pyrazolato groups each comprise a halogen or pseudo-halogen attached at the 4 position of the bridging pyrazole rings wherein said halogen or pseudo-halogen is selected from the group consisting of F, Cl, Br, I and CN.

14. The Fe(III) complex of claim 13, wherein said four ligands each comprise a terminal ligand selected from the group of F, Cl, Br, SCN, OCN, OPh, Ph, and py, where Ph is a phenyl group and py is a pyridine group.

15. The Fe(III) complex of claim 13, wherein said four ligands each comprise a bridging ligand selected from the group consisting of pyrazine and bipyridine.

16. The Fe(III) complex of claim 13, wherein said four ligands each comprise a metal.

17. The Fe(III) complex of claim 11, wherein the complex is given by the formula:

$$Fe_8\,(\mu_4\text{-}O)_4(\mu\text{-}pz)_{12}L_4$$

where the portion of the complex identified as $\mu_4$-O is a quadruply bridging oxygen atom and p-pz is a bridging pyrazole ring, and the portion of the complex identified as L is a ligand.

18. The Fe(III) complex of claim 11, wherein said Fe(III) complex comprises a contrast agent.

* * * * *